US005837455A

United States Patent [19]

Guesdon et al.

[11] Patent Number: 5,837,455

[45] Date of Patent: Nov. 17, 1998

[54] MYCOBACTERIAL NUCLEIC ACID HYBRIDIZATION PROBES AND METHODS OF USE

[75] Inventors: Jean-Luc Guesdon, Paris; Dominique Thierry, Boulogne; Agnès Ullmann, Paris; Brigitte Gicquel, Paris; Anne Brisson-Noel, Paris, all of France

[73] Assignee: Institut Pasteur, Paris, France

[21] Appl. No.: 487,645

[22] Filed: Jun. 7, 1995

Related U.S. Application Data

[63] Continuation of Ser. No. 829,016, filed as PCT/FR90/00591 Sep. 6, 1990, published as WO91/03558 Mar. 21, 1991, Pat. No. 5,597,911.

[30] Foreign Application Priority Data

| | | | |
|---|---|---|---|
| Sep. 6, 1989 | [FR] | France | 89 11665 |
| Mar. 2, 1990 | [FR] | France | 90 02676 |

[51] Int. Cl.[6] .......... C12N 15/00; C07H 21/02; C07H 21/04; C07H 21/00

[52] U.S. Cl. .......... 435/6; 435/320.1; 536/23.1; 536/24.3; 536/24.32; 536/25.32

[58] Field of Search .......... 536/23.1, 24.3, 536/24.32, 25.32; 435/320.1, 6

[56] References Cited

U.S. PATENT DOCUMENTS

| | | | |
|---|---|---|---|
| 5,168,039 | 12/1992 | Crawford et al. | 435/6 |
| 5,183,737 | 2/1993 | Crawford et al. | 435/6 |
| 5,370,998 | 12/1994 | Crawford et al. | 435/91.2 |
| 5,597,911 | 1/1997 | Guesdon et al. | 536/24.32 |
| 5,631,130 | 5/1997 | Leckie et al. | 435/6 |

FOREIGN PATENT DOCUMENTS

| | | | |
|---|---|---|---|
| WO9010085 | 9/1990 | WIPO | C12Q 1/68 |
| WO 96/04402 | 2/1996 | WIPO . | |

OTHER PUBLICATIONS

Eisenach et al. (1988) J. Clin. Microbiol. 26:2240–45.

Eisenach et al. (1986) Am. Review Respir. Dis. 133:1065–68.

Thierry et al. (1990) Nucl. Acids Res. 18:188.

Matthews et al. (1988) Anal. Biochem. 169:1–25.

Eisenach, Kathleen Davis, (1987) Ph.D. Dissertation Entitled "The Development of Moecular Probes for Mycobacterium Tuberculosis", abstract.

*Primary Examiner*—Kenneth R. Horlick
*Assistant Examiner*—Joyce Tung
*Attorney, Agent, or Firm*—Oblon, Spivak, McClelland, Maier & Neustadt, P.C.

[57] ABSTRACT

Fragments of nucleic acids derived from an appropriate mycobacteria genome, particularly *Mycobacterium tuberculosis,* their applications in the diagnosis of mycobacteria infections, as well as plasmides containing said fragments. The nucleotidic sequence is comprised of a nucleotidic sequence repeated in the genome of a mycobacterium and specific of the bacillus of tuberculosis and is characterized by a strong hybridation with *M. tuberculosis.*

11 Claims, 11 Drawing Sheets

```
        10         20         30         40         50         60
GTCGACACGC CTTCTGCACG GGAAGTCCTT CTGCGGCCAT CGTTGCTATG GCCGCTTACT
        70         80         90        100        110        120
GCCTTCTAGT CCGTGCGGCT CTCGCAACAG CTCACGGGAC CTTTTTGAGG ATCGCCACTT
       130        140        150        160        170        180
CAGGTCTTCA ACTCGCGGAT GCCCTCATTG GCAACGTTTG CGCCCTGCCT TGGGGCGGCC
       190        200        210        220        230        240
GGCAGCCACC AAGTCGAGCA CTTTGCGGCG GAACTACTCG GGGTAACACT TCGGCACGGA
       250        260        270        280        290        300
CACGGCTCGT TCGACGGACG TCGTGACCAG AAGTCGAGCA AACCGACTCC ACTCTAGCTA
       310        320        330        340        350        360
GTGATACAAG CTTTTTTGTA GCCGCGCGAT GAACCGCCCC GGCATGTCCG GAGACTCCAG
       370        380        390        400        410        420
TTCTTGGAAA GGATGGGGTC ATGTCAGGTG GTTCATCGAG GAGGTACCCC CCGGAGCTGC
       430        440        450 ISTB-1 460        470 IS-3  480
GTGAGCGGGC GGTGCGGATG GTCGCAGAGA TCCGCGGTCA GCACGATTCG GAGTGGGCAG
       490        500        510        520        530        540
CGATCAGTGA GGTCGCCCCT CTACTTGGTG TTGGCTGCGC GGAGACGGTG CGTAAGTGGG
       550        560        570        580        590 IS-1  600
TGCGCCAGGC GCAGGTCGAT GCCGGCGCAC GGCCCGGGAC CACGACCGAA GAATCCGCTG
```

FIG.8A

```
           610        620        630        640        650        660
      AGCTGAAGCG CTTAGCGGCG GGACAACGCC GAATTGCGAA GGGCGAACGC GATTTTAAAG
                                      ‾‾‾‾‾‾‾‾‾‾‾‾‾‾‾‾‾‾‾‾
           670        680        690 ˋISTB-3 700       710        720
      ACCGCGTCGG CTTTCTTCGC GGCCGAGCTC GACCGGCCAG CACGCTAATT AACGGTTCAT
                                                 ‾‾‾‾‾‾‾‾‾‾‾‾‾‾‾‾‾‾‾‾
           730        740        750        760 ˋISTB-7 770       780
      CGCCGATCAT CAGGGCCACC GCGAGGGCCC CGATGGTTTG CGGTGGGGTG TCGACTCGAT
                                                            ‾‾‾‾‾‾‾‾‾‾
                                                              ˋISTB-5
           790        800        810        820        830        840
      CTGCACACAG CTGACCGAGC TGGGTGTGCC GATCGCCCCA TCGACCTACT ACGACCACAT
      ‾‾‾‾‾‾‾‾‾‾            ‾‾‾‾‾‾‾‾‾‾‾‾‾‾‾‾‾‾‾‾ ‾‾‾‾‾‾‾‾‾‾‾‾‾‾‾‾‾‾‾‾
       ˋIS-6 850       860        870 ˋIS-4 880  ˋISTB-4 890       900
      CAACCGGGAG CCCAGCCGCC GCGAGCTGCG CGATGGCGAA CTCAAGGAGC ACATCAGCCG
                                                            ‾‾‾‾‾‾‾‾‾‾
           910        920        930        940        950        960
      CGTCCACGCC CCCAACTACG GTGTTTACGG TGCCCGCAAA GTGTGGCTAA CCCTGAACCG
      ‾‾‾‾‾‾‾‾‾‾‾‾‾‾‾‾‾‾‾‾‾                                 ‾‾‾‾‾‾‾‾‾‾
       ˋIS-2 970       980        990       1000 ˋISTB-6 1010      1020
      TGAGGGCATC GAGGTGGCCA GATGCACCGT CGAACGGCTG ATGACCAAAC TCGGCCTGTC
                           ‾‾‾‾‾‾‾‾‾‾‾‾‾‾‾‾‾‾‾‾ ‾‾‾‾‾‾‾‾‾‾
           1030       1040 ˋISTB-8 1050      1060 ˋISTB-2 1070      1080
      CGGGACCACC CGCGGCAAAG CCCGCAGGAC CACGATCGCT GATCCGGCCA CAGCCCGTCC
           1090       1100       1110       1120       1130       1140
      CGCCGATCTC GTCCAGCGCC GCTTCGGACC ACCAGCACCT AACCGGCTGT GGGTAGCAGA
           1150       1160       1170       1180       1190       1200
      CCTCACCTAT GTGTCGACCT GGGCAGGGTT CGCCTACGTG GCCTTTGTCA CCGACGCCTA
```

1210 1220 1230 1240 1250 1260

CGCTCGCAGG ATCCTGGGCT GGCGGGTCGC TTCCACGATG GCCACCTCCA TGGTCCTCGA 1270 1280 1290 1300 1310 1320

CGCGATCGAG CAAGCCATCT GGACCCGCCA ACAAGAAGGC GTACTCGACC TGAAAGACGT 1330 1340 1350 1360 1370 1380

TATCCACCAT ACGGATAGGG GATCTCAGTA CACATCGATC CGGTTCAGCG AGCGGCTCGC

ISTB-9

1390 1400 1410 1420 1430 1440

CGAGGCAGGC ATCCAACCGT CGGTCGGAGC GGTCGGAAGC TCCTATGACA ATGCACTAGC 1450 1460 1470 1480 1490 1500

CGAGACGATC AACGGCCTAT ACAAGACCGA GCTGATCAAA CCCGGCAAGC CCTGGCGGTC 1510 1520 1530 1540 1550 1560

CATCGAGGAT GTCGAGTTGG CCACCGCGCG CTGGGTCGAC TGGTTCAACC ATCGCCGCCT 1570 1580 1590 1600 1610 1620

CTACCAGTAC TGCGGCGACG TCCCGCCGGT CGAACTCGAG GCTGCCTACT ACGCTCAACG

IS-5 ISTB-10

1630 1640 1650 1660 1670 1680

CCAGAGACCA GCCGCCGGCT GAGGTCTCAG ATCAGAGAGT CTCCGGACTC ACCGGGGCGG

TTCA

FIG.8C

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 13 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

TGAACCGCCC CGG 13

( 2 ) INFORMATION FOR SEQ ID NO:2:

( i ) SEQUENCE CHARACTERISTICS:
( A ) LENGTH: 13 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:2:

CCGGGGCGGT TCA 13

( 2 ) INFORMATION FOR SEQ ID NO:3:

( i ) SEQUENCE CHARACTERISTICS:
( A ) LENGTH: 1684 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:3:

GTCGACACGC CTTCTGCACG GGAAGTCCTT CTGCGGCCAT CGTTGCTATG GCCGCTTACT 60

GCCTTCTAGT CCGTGCGGCT CTCGCAACAG CTCACGGGAC CTTTTTGAGG ATCGCCACTT 120

CAGGTCTTCA ACTCGCGGAT GCCCTCATTG GCAACGTTTG CGCCCTGCCT TGGGGCGGCC 180

GGCAGCCACC AAGTCGAGCA CTTTGCGGCG GAACTACTCG GGGTAACACT TCGGCACGGA 240

CACGGCTCGT TCGACGGACG TCGTGACCAG AAGTCGAGCA AACCGACTCC ACTCTAGCTA 300

GTGATACAAG CTTTTTTGTA GCCGCGCGAT GAACCGCCCC GGCATGTCCG GAGACTCCAG 360

TTCTTGGAAA GGATGGGGTC ATGTCAGGTG GTTCATCGAG GAGGTACCCG CCGGAGCTGC 420

GTGAGCGGGC GGTGCGGATG GTCGCAGAGA TCCGCGGTCA GCACGATTCG GAGTGGGCAG 480

CGATCAGTGA GGTCGCCCGT CTACTTGGTG TTGGCTGCGC GGAGACGGTG CGTAAGTGGG 540

TGCGCCAGGC GCAGGTCGAT GCCGGCGCAC GGCCCGGGAC CACGACCGAA GAATCCGCTG 600

AGCTGAAGCG CTTAGCGGCG GGACAACGCC GAATTGCGAA GGGCGAACGC GATTTTAAAG 660

ACCGCGTCGG CTTTCTTCGC GGCCGAGCTC GACCGGCCAG CACGCTAATT AACGGTTCAT 720

CGCCGATCAT CAGGGCCACC GCGAGGGCCC CGATGGTTTG CGGTGGGGTG TCGAGTCGAT 780

CTGCACACAG CTGACCGAGC TGGGTGTGCC GATCGCCCCA TCGACCTACT ACGACCACAT 840

CAACCGGGAG CCCAGCCGCC GCGAGCTGCG CGATGGCGAA CTCAAGGAGC ACATCAGCCG 900

CGTCCACGCC GCCAACTACG GTGTTTACGG TGCCCGCAAA GTGTGGCTAA CCCTGAACCG 960

TGAGGGCATC GAGGTGGCCA GATGCACCGT CGAACGGCTG ATGACCAAAC TCGGCCTGTC 1020

CGGGACCACC CGCGGCAAAG CCCGCAGGAC CACGATCGCT GATCCGGCCA CAGCCCGTCC 1080

CGCCGATCTC GTCCAGCGCC GCTTCGGACC ACCAGCACCT AACCGGCTGT GGGTAGCAGA 1140

-continued

| | | | | | | |
|---|---|---|---|---|---|---|
| CCTCACCTAT | GTGTCGACCT | GGGCAGGGTT | CGCCTACGTG | GCCTTTGTCA | CCGACGGCTA | 1200 |
| CGCTCGCAGG | ATCCTGGGCT | GGCGGGTCGC | TTCCACGATG | GCCACCTCCA | TGGTCCTCGA | 1260 |
| CGCGATCGAG | CAAGCCATCT | GGACCCGCCA | ACAAGAAGGC | GTACTCGACC | TGAAAGACGT | 1320 |
| TATCCACCAT | ACGGATAGGG | GATCTCAGTA | CACATCGATC | CGGTTCAGCG | AGCGGCTCGC | 1380 |
| CGAGGCAGGC | ATCCAACCGT | CGGTCGGAGC | GGTCGGAAGC | TCCTATGACA | ATGCACTAGC | 1440 |
| CGAGACGATC | AACGGCCTAT | ACAAGACCGA | GCTGATCAAA | CCCGGCAAGC | CCTGGCGGTC | 1500 |
| CATCGAGGAT | GTCGAGTTGG | CCACCGCGCG | CTGGGTCGAC | TGGTTCAACC | ATCGCCGCCT | 1560 |
| CTACCAGTAC | TGCGGCGACG | TCCCGCCGGT | CGAACTCGAG | GCTGCCTACT | ACGCTCAACG | 1620 |
| CCAGAGACCA | GCCGCCGGCT | GAGGTCTCAG | ATCAGAGAGT | CTCCGGACTC | ACCGGGGCGG | 1680 |
| TTCA | | | | | | 1684 |

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:4:

ATGTCAGGTG GTTCATCGAG 20

( 2 ) INFORMATION FOR SEQ ID NO:5:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:5:

ACAGGCCGAG TTTGGTCATC 20

( 2 ) INFORMATION FOR SEQ ID NO:6:

( i ) SEQUENCE CHARACTERISTICS:
( A ) LENGTH: 21 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:6:

TTCGCAATTC TGGCGTTGTC C 21

( 2 ) INFORMATION FOR SEQ ID NO:7:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:7:

TCGACCTACT ACGACCACAT 20

-continued ( 2 ) INFORMATION FOR SEQ ID NO:8:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:8:

G T C G A G T C G A   T C T G C A C A C A   2 0

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:9:

G T T C A G G G T T   A G C C A C A C T T   2 0

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:10:

C A G C A C G C T A   A T T A A C C C G G   2 0

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:11:

T G G C C A G A T G   C A C C G T C G A A   2 0

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:12:

A G T A C A C A T C   G A T C C G G T T C   2 0

( 2 ) INFORMATION FOR SEQ ID NO:13:

( i ) SEQUENCE CHARACTERISTICS:
( A ) LENGTH: 20 base pairs

-continued ( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:13:

TACTACGCTC AACGCCAGAG 20

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:14:

CATCAGCCGC GTCCACGCCG CCAACTACGG 30

( 2 ) INFORMATION FOR SEQ ID NO:15:

( i ) SEQUENCE CHARACTERISTICS:
( A ) LENGTH: 30 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:15:

TGTGCCGATC GCCCCATCGA CCTACTACGA 30

( 2 ) INFORMATION FOR SEQ ID NO:16:

( i ) SEQUENCE CHARACTERISTICS:
( A ) LENGTH: 30 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:16:

GTCGAGTCGA TCTGCACACA GCTGACCGAG 30

MYCOBACTERIAL NUCLEIC ACID HYBRIDIZATION PROBES AND METHODS OF USE

The present application is a continuation of U.S. Ser. No. 07/829,016, filed Apr. 14, 1992, now U.S. Pat. No. 5,597,911, which is a U.S. national stage application of International Application No. PCT/FR90/00591, filed Sep. 6, 1990, published as WO91/03558 Mar. 21, 1991.

BACKGROUND OF THE INVENTION

1. Field of the Invention

The present invention relates to nucleic acid fragments derived from the genome of an appropriate mycobacterium, in particular *Mycobacterium tuberculosis,* to their applications in the diagnosis of mycobacterial infections, and to plasmids containing the said fragments.

2. Description of the Background

Mycobacteria correspond to the Mycobacterium genus which comprises at least 54 different species.

Among them, about 10 are pathogenic or opportunistic for man or animals. Two of them, *M. tuberculosis* and *M. leprae* are the agents for tuberculosis and leprosy respectively.

It is known that these two diseases represent a major public health problem; indeed, there are currently between 15 and 60 million people afflicted by tuberculosis worldwide and 2 to 3 million people die each year as a result of this infection. *M. tuberculosis* is the most common cause of mycobacterial infections in developed countries. In France, $10^4$ new cases of tuberculosis appear each year. Vaccination using BCG (Bacille Calmette-Guérin, an attenuated strain of *M. bovis*) is far from being effective in the entire population. This efficacy ranges from about 80% in western countries such as England, to 0% in India (results of the last vaccination trial in Chingleput). Furthermore, the appearance of *M. tuberculosis* strains resistant to the usual antituberculotics and the existence of a correlation between tuberculosis and AIDS adds to the urgency of developing a rapid method of detection and identification of mycobacteria.

For example, an epidemiological study carried out in Florida has shown that 10% of AIDS patients suffer from tuberculosis at the time of the AIDS diagnosis or 18 months before it. In these patients, tuberculosis appears in 60% of cases in a disseminated form which is therefore undetectable by conventional diagnostic tests such as pulmonary radiography or sputum analysis.

Finally, the diagnosis of tuberculosis and other related mycobacterioses is difficult to carry out for various reasons: the pulmonary diseases caused by various mycobacteria cannot be clinically, radiologically or histologically differentiated; mycobacteria are often present at low levels and when they are at levels detectable by the conventional methods used, the disease has already developed and the patients are contagious to others; furthermore, because of the very long generation time in these bacteria (24 h for *M. tuberculosis* compared with 20 min for *E. coli*), the culture of these organisms is difficult. Thus, 6 to 8 weeks are required in order to identify the microbes and more time is required in order to obtain an antibiogram which can be used for the appropriate treatment of the patients. It is therefore essential to be able to have available a detection test which does not require the culture of microbes and which may be used directly with the pathological samples even when the microbes are present therein in low concentrations.

Several techniques are currently used clinically to identify a mycobacterial infection.

First, the direct microscopic detection of the microorganisms should be mentioned; this technique is rapid, but it does not permit identification of the mycobacterial species observed and it lacks sensitivity insofar as a large number of microorganisms must be present in the sample (>$10^4$/ml) in order to permit reliable detection (BATES J., CHEST, 1979, 76, (suppl.), 757–763).

The cultures, when they are positive, have a Specificity close to 100% and permit the identification of the mycobacterial species isolated; however, as specified above, the growth of the mycobacteria in vitro can only be achieved in 3 to 6 weeks and when few mycobacteria are present at the infection site, repeated cultures are required in order to ensure a correct result (BATES J., 1979 and BATES J. et al., Am. Rev. Respir. Dis., 1986, 134, 415–417).

Serological techniques may prove to be advantageous under certain conditions but their use is limited by their low sensitivity and/or specificity (DANIEL T. M. et al., Am. Rev. Respir. Dis., 1987, 135, 1137–1151).

The presence or absence of mycobacteria may also be determined by hybridisation to DNA or RNA using probes which are specific for the DNA sequences (KIEHN T. E. et al., J. Clin. Microbiol., 1987, 25, 1551–1552; ROBERTS M. C. et al., J. Clin. Microbiol., 1987, 25, 1239–1243; DRAKE T. A. et al., J. Clin. Microbiol., 1987, 25, 1442–1445). However, these methods are based on the nucleotide sequence polymorphism of the fragments used or on the polymorphism of the adjacent regions and also require the culture of microorganisms.

Some DNA sequences of various mycobacteria and, in particular, some mycobacterial antigen-encoding genes have been described. There may be mentioned in particular International Application PCT WO 88/00974 whose inventor is YOUNG R. and whose content is taken up in an article which appeared in Nature, 1985, 316, 450; these publications describe the genes encoding five immunodominant *M. leprae* antigens, and in particular the gene encoding the 65-kDA antigen has been sequenced. International Application PCT WO 88/05823 may also be mentioned, whose co-inventors are HUSSON R., YOUNG R. and SHINNICK T. and whose content is taken up in the article which appeared in J. Bact., 1987, 169, 1080–1088 and which describes the *M. tuberculosis* genes encoding protein antigens and, in particular, the 65-kDa antigen. This International Application specifies, in particular, that the *M. tuberculosis* genes encoding five immunologically active proteins were isolated by systematic screening of a recombinant DNA library which is expressed in a bacteriophage lambda gt11, with a collection of monoclonal antibodies directed against the protein antigens of this bacteria. One of the *M. tuberculosis* antigens, a 65-kDa protein, possesses determinants common to *M. tuberculosis* and *M. leprae.*

International Application PCT WO 88/06591, whose co-inventor is in particular T. SHINNICK, describes a 540-amino acid recombinant protein (65-kDa protein) as well as the DNA sequence and the expression vectors of the said protein, and the applications of the said recombinant protein. This application also describes peptides corresponding to sequences of this protein, and their applications.

The genes encoding proteins of other mycobacteria (*M. africanum, M. smegmatis, M. bovis* BCG and *M. avium*) have also been isolated. THOLE et al. (Infect. Immunol., 1987, 55, 1466–1475), who have described a 64-kDa *M. bovis* BCG protein expressed in *E. coli*, may be mentioned in particular.

However, the amount of mycobacterial DNA present in most biological samples is not sufficient to give a positive signal; the technique of hybridisation therefore proved inappropriate for the detection of mycobacterial DNA extracted directly from biological samples.

A certain number of studies have also shown some structural homology between the various mycobacteria. However, differences in the DNA sequence of *M. tuberculosis* and *M. bovis* have been described in the 3' region of the open reading frame of the 65-kDa antigen (SHINNICK et al., 1987, THOLE et al., 1987), but a homologous region has not been observed in *M. leprae* DNA (MEHRA et al., Proc. Nat. Acad. Sci. USA, 1986, 83, 7013–7017, also PCT 88/000974).

Publications also exist which have demonstrated the existence of repetitive sequences in mycobacteria; in particular, the article by K. D. EISENACE et al. (J. Clin. Microbiol., 1988, 26, 11, 2240–2245) may be mentioned, which describes three cloned segments of *M. tuberculosis* DNA, which have been identified by selective hybridisation to *M. bovis* DNA. These three recombinant segments, termed M13KE37 (790 base pairs), M13KE49 (570 base pairs) and M13KE115 (about 1600 base pairs) respectively are obtained by cloning DNA fragments of *M. tuberculosis* inside the bacteriophage M13. However, this article reveals that the nucleotide sequence of the corresponding segments is not known to its authors.

The article by D. M. COLLINS et al. (FEMS Microbiol. Letters, 1989, 60, 175–178), which describes the identification of a repetitive DNA sequence specific to *M. paratuberculosis,* may also be mentioned.

Moreover, it is appropriate to mention the article by REDDI et al. (INTERNATIONAL JOURNAL OF LEPROSY, 1988, 56, No. 4, p. 592–598) which describes the existence inside the DNA of *Mycobacterium tuberculosis* H37Rv and H37Ra, of repetitive fragments whose sequence has not been determined. The repetitive fragments described by REDDI et al., which are 5.6 and 4.8 kb fragments respectively, are not specific to the tuberculosis bacillus group since they are also present in *M. kansasii* which does not belong to the tuberculosis complex.

The following additional references also constitute the state of the art prior to the present invention.

BAESS I., Acta Path. Microbiol. Scand., 1979, 87, 221–226; BEAUCAGE S. L. et al., Tetrahedron Lett., 1981, 22, 1859–1862; EISENACH K. D. et al., Am. Rev. Respir. Dis., 1986, 133, 1065–1068; GHEORGHIU M. et al., J. Biol. Standardization, 1988, 16, 15–26; GLASSROTH J. et al., N. Engl. J. Med., 1980, 302, 1441–1450; HAWKINS C. C. et al., Ann. Intern. Med., 1985, 105, 184–188; IMAEDA T., Int. J. Systematic Bacteriol., 1985, 35, 147–150; IMAEDA T. et al., Int. J. Systematic Bacteriol., 1988, 38, 151–156; KOGAN S. C. et al., N. Engl. J. Med., 1987, 317, 985–990; LI H. et al., Nature (Lond.), 1988, 335, 414–417; LU M. C. et al., Infect. Immun., 1987, 55, 2378–2382; MANIATIS T. et al., 1982, Cold Spring Harbor, N.Y.; McFADDEN J. J. et al., Mol. Microbiol., 1987, 1, 283–291; PAO C. C. et al., Tubercle, 1988, 69, 27–36; PATEL R., J. Gen. Microbiol., 1986, 132, 541–551; SAIKI R. K. et al., Science, 1988, 239, 487–491; SANGER F. et al., Proc. Natl. Acad. Sci. USA, 1977, 74, 5463–5467; SMIDA J. et al., Int. J. Leprosy, 1988, 56, 449–454; THEIN S. L. et al., in Human Genetic Diseases, 1986, IRL Press, 33–50; THOLE J. E. R. et al., Infect. Immun., 1985, 50, 800–806; WATSON E. A., Canad. J. Pub. Health, 1935, 26, 268–275; WOLINSKY E., Am. Rev. Respir. Dis. 1979, 119, 107–159.

Recently, a method of detection of low amounts of mycobacteria by amplification and hybridisation directly on biological samples has been developed; the said method uses the nucleotide sequence polymorphism of a gene fragment common to all mycobacteria, and in particular a fragment of the gene encoding the 65-kD protein (French Patent Application No. 89 05057).

SUMMARY OF THE INVENTION

BRIEF DESCRIPTION OF THE DRAWINGS

FIG. 8 shows the positions of the primers and probes of formulae IV to XVI with respect to the complete sequence of formula III.

DETAILED DESCRIPTION OF THE PREFERRED EMBODIMENTS

Figure 1:
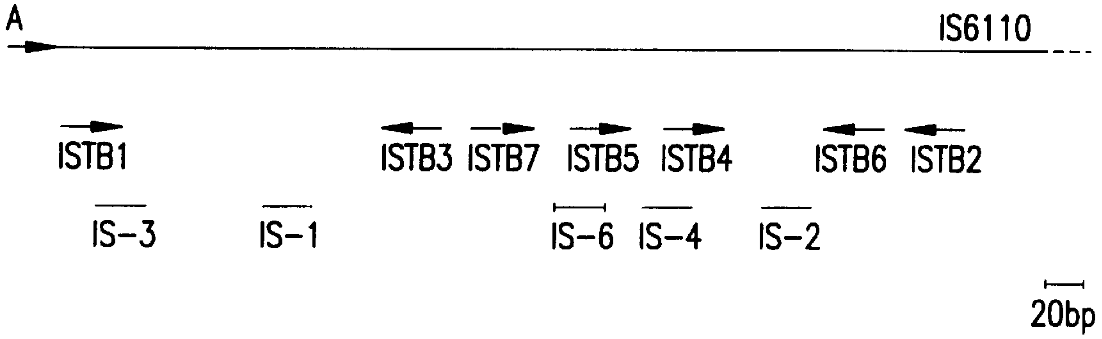
FIG. 1 shows the location of primers and probes in the sequence IS6110.

Continuing the work on mycobacteria in this direction, the inventors have developed a detection method which is specific and even more rapid as it enables a mycobacterium of a determined group to be identified in a biological sample in less than 24 hours.

Accordingly, the object of the present invention is to provide a method of detection and/or identification which is specific for at least one group of mycobacteria, in particular which is specific for the tuberculosis bacillus group, enabling the detection of small amounts of DNA extracted from microbes which are themselves small in number and revealing the presence of mycobacteria of the group(s) to be detected, directly in the pathological samples.

An object of the invention is also to provide diagnostic reagents which are specific for the mycobacteria group and in particular for the tuberculosis bacillus group.

The subject of the present invention is a nucleotide sequence derived from mycobacteria, characterised in that it consists of a repetitive nucleotide sequence in the genome of a mycobacterium and which is specific for the tuberculosis bacillus group, and in that it hybridises very strongly to *M. tuberculosis.*

In the present invention, tuberculosis bacillus group refers to the group which comprises *M. bovis*-BCG, *M. bovis, M. tuberculosis, M. africanum* and *M. microti.*

In the present invention, nucleotide sequence is understood to mean a double-stranded DNA sequence, a single-stranded DNA sequence as well as the products of transcription of the said sequences.

Within the context of the present invention, strong hybridisation is understood to mean a hybridisation giving a high signal linked to the number of repetitive sequences present in the genomic DNA; a high signal makes it possible to obtain a spot which is easily visible with the naked eye after autoradiography of short duration, carried out under the conditions defined in Example 1 below, in particular not more than one hour; for example, a very intense spot is obtained with *M. tuberculosis* after an autoradiography of about one hour when a labelled probe having a specific activity of close to $10^9$ cmp per $\mu$g of DNA is used, whereas for *M. bovis* BCG, a weak signal is obtained and this only after a period of 48 hours.

According to a preferred embodiment of the said sequence, it comprises at its 5' end the sequence 5'TGAACCGCCCCGG 3' of formula I (SEQ ID NO:1) and at its 3' end the sequence 5'CCGGGGCGGTTCA 3' of formula II (SEQ ID NO:2), the said sequence containing in addition at least one fragment of a sequence of the following formula III (SEQ ID NO:3):

FORMULA III

| 10 | 20 | 30 | 40 | 50 | 60 |
|---|---|---|---|---|---|
| GTCGACACGC | CTTCTGCACG | GGAAGTCCTT | CTGCGGCCAT | CGTTGCTATG | GCCGCTTACT |
| 70 | 80 | 90 | 100 | 110 | 120 |
| GCCTTCTAGT | CCGTGCGGCT | CTCGCAACAG | CTCACGGGAC | CTTTTTGAGG | ATCGCCACTT |
| 130 | 140 | 150 | 160 | 170 | 180 |
| CAGGTCTTCA | ACTCGCGGAT | GCCCTCATTG | GCAACGTTTG | CGCCCTGCCT | TGGGGCGGCC |
| 190 | 200 | 210 | 220 | 230 | 240 |
| GGCAGCCACC | AAGTCGAGCA | CTTTGCGGCG | GAACTACTCG | GGGTAACACT | TCGGCACGGA |
| 250 | 260 | 270 | 280 | 290 | 300 |
| CACGGCTCGT | TCGACGGACG | TCGTGACCAG | AAGTCGAGCA | AACCGACTCC | ACTCTAGCTA |
| 310 | 320 | 330 | 340 | 350 | 360 |
| GTGATACAAG | CTTTTTTGTA | GCCGCGCGAT | GAACCGCCCC | GGCATGTCCG | GAGACTCCAG |
| 370 | 380 | 390 | 400 | 410 | 420 |
| TTCTTGGAAA | GGATGGGGTC | ATGTCAGGTG | GTTCATCGAG | GAGGTACCCC | CCGGAGCTGC |
| 430 | 440 | 450 | 460 | 470 | 480 |
| GTGAGCGGGC | GGTGCGGATG | GTCGCAGAGA | TCCGCGGTCA | GCACGATTCG | GAGTGGGCAG |
| 490 | 500 | 510 | 520 | 530 | 540 |
| CGATCAGTGA | GGTCGCCCGT | CTACTTGGTG | TTGGCTGCGC | GGAGACGGTG | CGTAAGTGGG |
| 550 | 560 | 570 | 580 | 590 | 600 |
| TGCGCCAGGC | GCAGGTCGAT | GCCGGCGCAC | GGCCCGGGAC | CACGACCGAA | GAATCCGCTG |
| 610 | 620 | 630 | 640 | 650 | 660 |
| AGCTGAAGCG | CTTAGCGGCG | GGACAACGCC | GAATTGCGAA | GGGCGAACGC | GATTTTAAAG |
| 670 | 680 | 690 | 700 | 710 | 720 |
| ACCGCGTCGG | CTTTCTTCGC | GGCCGAGCTC | GACCGGCCAG | CACGCTAATT | AACGGTTCAT |
| 730 | 740 | 750 | 760 | 770 | 780 |
| CGCCGATCAT | CAGGGCCACC | GCGAGGGCCC | CGATGGTTTG | CGGTGGGGTG | TCGAGTCGAT |
| 790 | 800 | 810 | 820 | 830 | 840 |
| CTGCACACAG | CTGACCGAGC | TGGGTGTGCC | GATCGCCCCA | TCGACCTACT | ACGACCACAT |
| 850 | 860 | 870 | 880 | 890 | 900 |
| GAACCGGGAG | CCCAGCCGCC | GCGAGCTGCG | CGATGGCGAA | CTCAAGGAGC | ACATCAGCCG |
| 910 | 920 | 930 | 940 | 950 | 960 |
| CGTCCACGCC | GCCAACTACG | GTGTTTACGG | TGCCCGCAAA | GTGTGGCTAA | CCCTGAACCG |
| 970 | 980 | 990 | 1000 | 1010 | 1020 |
| TGAGGGCATC | GAGGTGGCCA | GATGCACCGT | CGAACGGCTG | ATGACCAAAC | TCGGCCTGTC |
| 1030 | 1040 | 1050 | 1060 | 1070 | 1080 |
| CGGGACCACC | CGCGGCAAAG | CCCGCAGGAC | CACGATCGCT | GATCCGGCCA | CAGCCCGTCC |
| 1090 | 1100 | 1110 | 1120 | 1130 | 1140 |
| CGCCGATCTC | GTCCAGCGCC | GCTTCGGACC | ACCAGCACCT | AACCGGCTGT | GGGTAGCAGA |
| 1150 | 1160 | 1170 | 1180 | 1190 | 1200 |
| CCTCACCTAT | GTGTCGACCT | GGGCAGGGTT | CGCCTACGTG | GCCTTTGTCA | CCGACGGCTA |
| 1210 | 1220 | 1230 | 1240 | 1250 | 1260 |
| CGCTCGCAGG | ATCCTGGGCT | GGCGGGTCGC | TTCCACGATG | GCCACCTCCA | TGGTCCTCGA |

-continued

FORMULA III

```
      1270       1280       1290       1300       1310       1320
CGCGATCGAG CAAGCCATCT GGACCCGCCA ACAAGAAGGC GTACTCGACC TGAAAGACGT

      1330       1340       1350       1360       1370       1380
TATCCACCAT ACGGATAGGG GATCTCAGTA CACATCGATC CGGTTCAGCG AGCGGCTCGC

      1390       1400       1410       1420       1430       1440
CGAGGCAGGC ATCCAACCGT CGGTCGGAGC GGTCGGAAGC TCCTATGACA ATGCACTAGC

      1450       1460       1470       1480       1490       1500
CGAGACGATC AACGGCCTAT ACAAGACCGA GCTGATCAAA CCCGGCAAGC CCTCGCGGTC

      1510       1520       1530       1540       1550       1560
CATCGAGGAT GTCGAGTTGG CCACCGCGCG CTGGGTCGAC TGGTTCAACC ATCGCCGCCT

      1570       1580       1590       1600       1610       1620
CTACCAGTAC TGCGGCGACG TCCCGCCGGT CGAACTCGAG GCTGCCTACT ACGCTCAACG

      1630       1640       1650       1660       1670       1680
CCAGAGACCA GCCGCCGGCT GAGGTCTCAG ATCAGAGAGT CTCCGGACTC ACCGGGGCGG

TTCA
```

According to an advantageous variant of this arrangement, the said nucleotide sequence comprises the nucleotides 343–1152 of the sequence of formula III above and fragments thereof, as well as sequences which present at least 80% homology with the said sequence or fragments thereof.

According to another advantageous variant of this arrangement, the said nucleotide sequence comprises the nucleotides 327–1684 of the sequence of formula III above and fragments thereof, as well as sequences which present at least 80% homology with the said nucleotide sequence or fragments thereof. The latter sequence has been termed IS6110 by the inventors and comprises in particular the following restriction sites: SalI, SmaI, KpnI and HindIII.

The present invention also includes nucleotide fragments, in particular oligonucleotides, derived from nucleotide sequences such as defined above, and in particular the following oligonucleotides, which are characterised in that they possess the sequences of formulae IV to XIII and A to H below, which are in addition identified by the designations which have been assigned to them by the inventors:

ISTB-1: 5' ATGTCAGGTGGTTCATCGAG 3' (IV) (SEQ ID NO:4)

ISTB-2: 5' ACAGGCCGAGTTTGGTCATC 3' (V) (SEQ ID NO:5)

ISTB-3: 5' TTCGCAATTCTGGCGTTGTCC 3' (VI) (SEQ ID NO:6)

ISTB-4: 5' TCGACCTACTACGACCACAT 3' (VII) (SEQ ID NO:7)

ISTB-5: 5' GTCGAGTCGATCTGCACACA 3' (VIII) (SEQ ID NO:8)

ISTB-6: 5' GTTCAGGGTTAGCCACACTT 3' (IX) (SEQ ID NO:9)

ISTB-7: 5' CAGCACGCTAATTAACCCGG 3' (X) (SEQ ID NO:10)

ISTB-8: 5' TGGCCAGATGCACCGTCGAA 3' (XI) (SEQ ID NO:11)

ISTB-9: 5' AGTACACATCGATCCGGTTC 3' (XII) (SEQ ID NO:12)

ISTB-1: 5' TACTACGCTCAACGCCAGAG 3' (XIII) (SEQ ID NO:13)

IS-2: 5' CATCAGCCGCGTCCACGCCGCCAACTACGG 3' (XIV) (SEQ ID NO:14)

IS-4: 5' TGTGCCGATCGCCCCATCGACCTACTACGA 3' (XV) (SEQ ID NO:15)

IS-6: 5' GTCGAGTCGATCTGCACACAGCTGACCGAG 3' (XVI) (SEQ ID NO:16)

as well as sequences which present at least 80% homology with any one of these fragments.

The invention also relates to nucleotide fragments which are complementary to those above and to fragments which are modified, in comparison with those above, by the removal or addition of nucleotide(s) in a proportion of about 15% relative to the length of the above fragments, and/or which are modified with respect to the nature of the nucleotides, provided that the modified nucleotide fragments preserve the capacity to hybridise to the mycobacterial DNA sequence which is analogous to that possessed by the corresponding unmodified fragments.

The subject of the present invention is also products of translation and/or fragments thereof, characterised in that they are encoded by a nucleotide sequence or a nucleotide sequence fragment conforming to the invention.

The subject of the present invention is furthermore a method of detection of a repetitive sequence which is specific for the tuberculosis bacillus group, characterised in that it comprises:

(1) a step in which a recombinant cosmid library is produced containing DNA fragments larger than 30 kb from a suitable mycobacterium; and (2) a step in which the cosmid clone(s) containing at least one repetitive sequence is/are detected by hybridisation to an appropriately labelled total genomic DNA from a suitable mycobacterium.

Visualisation of the hybrids formed allows the rapid detection of the repetitive sequences present in the genome of the said mycobacteria.

The subject of the present invention is also diagnostic reagents for the detection of at least one group of mycobacteria, characterised in that they comprise at least one nucleotide sequence or a fragment thereof, as defined above, for the detection of mycobacteria of the tuberculosis bacillus group, optionally combined with at least one other nucleotide sequence which is suitable for the detection of another group of mycobacteria and/or at least one suitable marker.

Such a reagent allows for example the simultaneous detection of a mycobacterium of the tuberculosis bacillus group and a mycobacterium of the MAIP (*M. avium, M. intracellulare, M. paratuberculosis*) group.

According to an advantageous embodiment of the said reagents, they consist of pairs of primers for the synthesis of a DNA or RNA fragment of the tuberculosis bacillus group, each primer comprising a nucleotide sequence or a nucleotide sequence fragment as defined above.

According to an advantageous form of this embodiment, a pair of primers conforming to the invention consists in particular of an oligonucleotide of formula IV paired with an oligonucleotide of formula V.

These primers allow in particular the synthesis of the nucleotide sequence of formula III above and/or of its complementary strand and/or of the sequence IS6110.

According to another advantageous embodiment of the said reagents, they consist of a probe for detecting a DNA or RNA fragment from the tuberculosis bacillus group.

According to an advantageous form of this embodiment, the said detection probe advantageously comprises a nucleotide sequence of formula III for the detection of a mycobacterium of the tuberculosis bacillus group.

According to another advantageous embodiment, the marker is chosen from the group comprising in particular radioactive isotopes, suitable enzymes, fluorochromes, suitable chemical markers, haptens and antibodies or base analogues such as those described in French Patent No. 2,518,755 or European Patent Application No. 158,758.

The said reagents may be used in a very large number of diagnostic techniques based on the detection of nucleic acids by hybridisation; in particular, a probe conforming to the invention such as the sequence of formula III allows in particular the specific detection of the DNA of a mycobacterium of the tuberculosis bacillus group, and in particular *Mycobacterium tuberculosis.*

The subject of the present invention is also a family of recombinant plasmids, characterised in that they contain at least one nucleotide sequence conforming to the invention.

According to an advantageous embodiment of the said plasmid, it comprises the nucleotide sequence of formula III or a fragment thereof.

According to a preferred disposition of the said embodiment, the said plasmid comprises the said sequence combined with a vector pUC18.

This recombinant plasmid has been termed pMT01 by the inventors.

In accordance with the invention, the said recombinant plasmid was deposited under the No. I-900 on 25 Aug. 1989, in the Collection Nationale de Cultures de Microorganismes held by the Institut Pasteur 25 Rue du Docteur Roux, 75724 Paris, Cedex 15, in accordance with the provisions of the Budapest Treaty.

The subject of the present invention is also a method of rapid detection and identification of at least one group and/or one species of mycobacteria in a biological sample, characterised in that it comprises:

(1) a step in which the biological sample is brought into contact with at least one diagnostic reagent conforming to the invention, and (2) a step in which the product(s) resulting from the interaction between the nucleotide sequence of mycobacterium which may be present and the diagnostic reagent is detected by any suitable means.

According to an advantageous embodiment of this method, the diagnostic reagent(s) in step (1) is/are pair(s) of primers conforming to the invention and allowing the production of amplification products of the nucleotide sequence which is to be detected.

The amplification step is in particular one of the genetic amplification techniques such as the so-called Qβ replicase method (LIZARDI P. M. et al., Biotechnol., 1988, 6) or the so-called P.C.R. method (polymerase chain reaction) described in European Patent Applications No. 200,363, No. 201,184 and No. 229,701 filed by CETUS CO.

According to an advantageous form of this embodiment, the amplification products obtained in (1) are detected by electrophoretic separation.

For example, if the presence is observed of a DNA fragment migrating to the expected position, it can be concluded that the sample analysed contains DNA from the group of mycobacteria to be detected.

According to another advantageous form of this embodiment, the amplification products obtained in (1) are detected by hybridisation between the said amplification products and a suitably labelled diagnostic reagent conforming to the invention.

Such a method has the advantage of making it possible to produce a sensitive and specific test, which is direct and rapid (less than 24 hours), for the detection of at least one group of mycobacteria.

According to a particularly advantageous embodiment of this method for detecting the presence of *Mycobacterium tuberculosis* in a biological sample, it comprises the following steps:

i) bringing into contact the biological sample with a pair of nucleic acid fragments, called primers, according to the invention, the DNA contained in the sample having been, where appropriate, made accessible for the hybridisation beforehand and allowing, under these conditions, hybridisation of the *Mycobacterium tuberculosis* DNA;

ii) amplification of the *Mycobacterium tuberculosis* DNA;

iii) demonstrating the amplification of the DNA fragments corresponding to the fragment flanked by the primers, for example by gel electrophoresis;

iv) optional verification of the sequence of the amplified fragment, for example by specific probe hybridisation, sequencing or restriction site analysis.

According to another embodiment of the method of in vitro diagnosis of a mycobacterial infection in a specific biological sample, it comprises the steps of:

a) bringing the mycobacterial nucleic acid which may be present, in the biological sample tested, under conditions allowing accessibility in the form of single-stranded DNA, into contact with at least one pair of nucleotide primers according to the invention, it being possible for the said primers to hybridise to the mycobacterial nucleic acid if it is present, and to initiate the synthesis of the elongation product of the said primers, each strand of mycobacterial DNA fragment serving as a template when it is paired with the primers;

b) separating the synthesised DNA strands from their template;

c) repeating the synthesis of the elongation product using each DNA strand present at the end of step b) and capable of hybridising to the primers, until sufficient amplification of the desired DNA is obtained in order to be detected;

d) bringing the product from step c) into contact with a nucleotide probe under conditions enabling the presence of the desired amplified DNA fragment to be detected;

e) detecting the hybridisation products which may be formed.

According to a preferred embodiment of the in vitro diagnostic method defined above, the bringing into contact of the test sample is preceded by a step for treating the sample in order to extract the nucleic acid therefrom.

According to another preferred embodiment, the method comprises a step prior to bringing into contact with the primers, consisting of a treatment of the nucleic acid in the sample with a reverse transcriptase in order to obtain the synthesis of cDNA from the RNA which may be present in the test sample.

Some of the fragments conforming to the invention have the quite remarkable advantage of being usable as primers allowing the amplification of DNA fragments of the sequence of formula III, from mycobacteria, in particular of the tuberculosis bacillus group.

These primers for the amplification of mycobacterial DNA fragments, in particular for the amplification of fragments of the above-described sequence from *Mycobacterium tuberculosis,* are characterised in that they correspond to nucleotide fragments defined above, chosen from the following group or from the nucleotide fragments which are complementary to the following, or alternatively to modified but nevertheless functional fragments with respect to their capacity to hybridise to the said mycobacterial DNA fragment for the purpose of its amplification:

ISTB-1: 5' ATGTCAGGTGGTTCATCGAG 3' (IV) (SEQ ID NO:4)
ISTB-2: 5' ACAGGCCGAGTTTGGTCATC 3' (V) (SEQ ID NO:5)
ISTB-3: 5'TTCGCAATTCTGGCGTTGTCC 3' (VI) (SEQ ID NO:6)
ISTB-4: 5' TCGACCTACTACGACCACAT 3' (VII) (SEQ ID NO:7)
ISTB-5: 5' GTCGAGTCGATCTGCACACA 3' (VIII) (SEQ ID NO:8)
ISTB-6: 5' GTTCAGGGTTAGCCACACTT 3' (IX) (SEQ ID NO:9)
ISTB-7: 5' CAGCACGCTAATTAACCCGG 3' (X) (SEQ ID NO:10)
ISTB-8: 5' TGGCCAGATGCACCGTCGAA 3' (XI) (SEQ ID NO:11)
ISTB-9: 5' AGTACACATCGATCCGGTTC 3' (XII) (SEQ ID NO:12)
ISTB-10: 5' TACTACGCTCAACGCCAGAG 3' (XIII) (SEQ ID NO:13)

In a completely advantageous manner, and within the framework of their application to the amplification of DNA fragments, these primers are taken in pairs in order to hybridise under specific conditions to the respective 5' and 3' ends of the selected fragment of DNA to be amplified.

Various combinations of these primers make it possible to amplify DNA fragments of less than 350 base pairs in size, in particular less than 300 base pairs. This is particularly advantageous since the shorter the amplified fragment, the better the amplification.

According to a preferred embodiment of the invention, the primers for amplifying DNA fragments corresponding to the above definitions are further characterised in that they are chosen from the following pairs of primers:

ISTB2 and ISTB4:
5' ACAGGCCGAGTTTGGTCATG 3' (V) (SEQ ID NO: 5)

and

5' TCGACCTACTACGACCACAT 3' (VII) (SEQ ID NO: 8)

ISTB2 and ISTB5:

-continued

5' ACAGGCCGAGTTTGGTCATG 3' (V) (SEQ ID NO: 5)

5' GTCGAGTCGATCTGCACACA 3' (VIII) (SEQ ID NO: 9)

ISTB2 and ISTB7:
5' ACAGGCCGAGTTTGGTCATG 3' (V) (SEQ ID NO: 5)

and

ISTB7:
5' CAGCACGCTAATTAACCCGG 3' (X) (SEQ ID NO: 10)

ISTB5 and ISTB6:
5' GTCGAGTCGATCTGCACACA 3' (VIII) (SEQ ID NO: 8)

and

ISTB6:
5' GTTGACGGTTAGCCACACTT 3' (IX) (SEQ ID NO: 9)

ISTB6 and ISTB7:
ISTB6:
5' GTTCAGGGTTAGCCACACTT 3' (IX) (SEQ ID NO: 9)

and

ISTB7:
5' CAGCACGCTAATTAACCCGG 3' (X) (SEQ ID NO: 10)

A particularly advantageous pair of primers for carrying out the desired amplification is the pair of primers consisting of ISTB2 and ISTB7, given its specificity for the tuberculosis group of mycobacteria.

As shown in the attached FIG. 1, the specified pair of primers direct the amplification of fragments having the following lengths respectively:

ISTB1+ISTB3 direct the amplification of a 260 pb fragment,
ISTB2+ISTB4 direct the amplification of a 198 pb fragment,
ISTB2+ISTB5 direct the amplification of a 248 pb fragment,
ISTB5+ISTB6 direct the amplification of a 189 pb fragment,
ISTB6+ISTB7 direct the amplification of a 260 pb fragment,
ISTB2+ISTB7 direct the amplification of a 325 pb fragment.

The tests carried out in order to evaluate the amplification efficiency obtained using the above-described pairs (combinations) of primers show that this efficiency is completely satisfactory for the last five pairs of primers defined, all the more so since the amplifications were carried out on dilutions containing 10 ng, 10 pg and 10 fg of purified *M. tuberculosis* DNA, which shows that the amplification can be carried out using extremely low levels of DNA.

Another advantage of the primers proposed in the present invention lies in the specificity of the various pairs proposed.

In particular, some pairs of primers make it possible to differentiate between an infection due to mycobacteria of the tuberculosis group or an infection due to atypical bacteria. Thus, a test using various pairs of primers has been carried out on purified DNA from 19 mycobacterial species comprising: *M. tuberculosis, M. africanum, M. bovis, M. bovis* BCG, *M. microti* (these five species form the tuberculosis group), *M. gordonae, M. kansasii, M. malmoense, M. marinum, M. paratuberculosis, M. scrofulaceum, M. simiae, M. szulgai, M. terrae, M. xenopi, M. asiaticum, M. avium, M. chelonae* and *M. flavescens.*

For example, the pair ISTB2/ISTB7, and the pair ISTB1/ISTB2, detect only mycobacteria of the tuberculosis group and not atypical mycobacteria.

In accordance with the invention, the primers defined above are advantageously labelled with a chemical, physical or enzymatic marker and/or are fixed onto a solid support in particular a particulate or membranous support, for example magnetic beads.

According to another advantageous embodiment of the method conforming to the invention, the diagnostic reagent in step (1) is a detection probe conforming to the invention and enables hybrids to be obtained between the nucleotide sequence to be detected and the said probe.

The probes, conforming to the invention, for detecting amplified mycobacterial DNA fragments, are characterised in that they are nucleotide fragments which are specific for the sequence of formula III, fragments of which it is sought to detect, chosen from the nucleotide fragments belonging to the group of those that have been defined above, which are capable of hybridising to the said amplified DNA fragment, the said fragments being either labelled at their 5' and/or 3' end with a detectable substance, or fixed to a physical support.

As already stated above, the markers are advantageously chosen from radioactive isotopes, enzymes or suitable chemical markers, fluorochromes, haptens, antibodies, base analogues or alternatively a physical marker.

The fixing onto a support may be performed on a particulate or membranous solid support, for example magnetic beads.

Such nucleotide fragments should be capable of hybridising to the amplified DNA fragment, and when they are labelled with a detectable substance, they should demonstrate the existence of an infection by mycobacteria, and in particular those of the tuberculosis group.

Probes which are particularly preferred for implementing the invention are chosen from the following nucleotide fragments:

IS-2 (SEQ ID NO:14): 5' CATCAGCCGCGTCCACGCCGCCAACTACGG 3'

IS-4 (SEQ ID NO:15): 5' TGTGCCGATCGCCCCATCGACCTACTACGA 3'

IS-6 (SEQ ID NO:16): 5' GTCGAGTCGATCTGCACACAGCTGACCGAG 3'

The probes IS-2 and IS-4 are 30 bases in size and are complementary to the fragments amplified by means of the pairs of primers ISTB2/ISTB4, ISTB2/ISTB5, ISTB5/ISTB6, ISTB6/ISTB7 and ISTB2/ISTB7.

The probe IS-6 is also complementary to the fragment amplified by means of the pair of primers ISTB2/ISTB4.

These probes advantageously allow the detection of all the members of the tuberculosis mycobacteria group. They also have the advantage for the last four pairs of primers mentioned, of being capable of being used simultaneously, one serving as capture probe and the other as labelling probe.

They therefore allow direct detection to be carried out on a biological sample in a liquid medium.

When the probes are used as labelling probes, the marker may be chosen from the group comprising radioactive isotopes, suitable enzymes, fluorochromes or suitable chemical or chemiluminescent markers, haptens and antibodies or base analogues such as those described in French Patent No. 2,518,755 or European Patent Application 158 758, or alternatively physical markers.

Preferred markers are for example radioactive phosphorus ($^{32}P$) which is incorporated at the 5' end.

When the probes are used to capture, they are advantageously fixed onto a solid support as described above.

The sequence IS6110 also enables the species of a mycobacterium to be identified within the tuberculosis bacillus group, starting with a pure culture.

The subject of the present invention is furthermore a kit, box or a coordinated set ready for use, for implementing the method for detecting at least one mycobacterial group conforming to the invention, characterised in that it comprises, in addition to the required amounts of suitable buffers and reagents for implementing the said detection:

suitable doses of at least one pair of primers conforming to the invention; and/or suitable doses of at least one probe or one nucleotide probe fragment conforming to the invention.

According to an advantageous embodiment of the kit or outfit conforming to the present invention, the latter contains the following elements:

a pair of nucleic acid fragments consisting of two sequences selected from the ISTB sequences defined above;

the reagents required for carrying out a DNA amplification;

optionally, a component enabling the sequence of the amplified fragment to be checked, more particularly, a nucleic acid probe at least 20 bases in length which is capable of hybridising to a part of the IS6110 sequence situated between the two fragments of the abovementioned pair.

According to another advantageous embodiment of the kit for the in vitro diagnosis of a mycobacterial infection, in a specific biological sample, it comprises:

at least one pair of nucleotide primers corresponding to the definitions given above, which is capable of hybridising the 5' and 3' ends of a DNA fragment specific to mycobacteria, reagents required for the extraction of nucleic acids from the treated sample, reagents for carrying out the polymerisation of the said DNA fragment, using nucleotide primers, in particular polymerisation enzymes, in an amount sufficient to carry out the amplification of the DNA fragment which it is desired to amplify, at least one nucleotide fragment which may be used as a probe and which is capable of hybridising, under specific conditions, to the amplified DNA fragment, an internal standard for the amplification reaction, for example consisting of a DNA fragment optionally carried by a plasmid, it being possible for the said fragment to be easily detected by hybridisation, for example in that it contains a gene for resistance to an antibiotic, the said fragment being in addition provided at its two ends with at least one amplification primer, these primers being preferably chosen from the primers of the invention, a probe capable of hybridising to the DNA fragment contained in the internal standard, where appropriate, a reverse transcriptase for obtaining cDNA from RNA which may be present in the test sample, where appropriate, means for visualising the hybridisation.

Any sample of biological fluid or of biological tissue such as for example blood, serum, cephalorachidian liquid, pleural liquid, urine, sputum, samples obtained by bronchial tubage or aspiration, puncture or biopsy of the liver, ganglionic biopsy and the like, may be used as biological sample.

The diagnostic kit according to the invention has the advantage of being usable directly on clinical samples and enables results to be obtained in a very short time.

The presence of an internal standard which is added to the sample allows the presence of "false negatives" to be detected among the samples. Indeed, when the specific probe of the internal standard does not detect an amplification product, it is very likely that the sample contains a DNA polymerase inhibitor, an inhibitor which prevents the amplification of mycobacterial DNA or cDNA. In this case, various dilutions of the test sample can enable the presence of mycobacterial nucleic acid to be demonstrated.

When the internal standard exhibits a positive reaction, a negative reaction in the test sample makes it possible to deduce that mycobacteria are indeed absent.

It should be noted that the primers incorporated in the internal standard are not necessarily those of the invention. However, the choice of other primers may lead to a reduction in sensitivity.

According to a preferred embodiment of the diagnostic kit of the invention, the primers used are ISTB2 and ISTB7 and the probe for detecting the possible amplification product is IS-2 optionally combined with IS-6.

Advantageously, several detection probes may be used and, in particular, IS-6 may be added to IS-2.

The invention also relates to the production of nucleotide fragments according to the invention, whether they are derived from the sequence IS6110 as purified from tuberculosis mycobacteria, or whether they are chemically synthesised.

The phosphotriester method as described by NARANG S. A. et al. in Meth. of Enzymol., (1979), 68, 90, may be mentioned as an example of the synthesis of such nucleic acid fragments. Another suitable method for the preparation of nucleotide fragments is the phosphodiester method as described by BROWN E. L. et al. in Meth. Enzymol., (1979), 68, 109.

This preparation may also be carried out using an automated process, for example involving diethylphosphoramidites as starting constituents, and in this case, the synthesis may be carried out according to the description by BEAUCAGE et al., Tetrahedron Letters, (1981), 22, 1859–1862.

In addition to the above arrangements, the invention further comprises other arrangements which will emerge from the following description which refer to exemplary embodiments of the method which is the subject of the present invention.

It should be understood however that these examples are given solely as an illustration of the subject of the invention without in any way constituting a limitation thereof.

EXAMPLE 1

Detection of Mycobacteria of the Tuberculosis Bacillus Group a) Construction of the *M. tuberculosis* genomic library The genomic DNA from *M. tuberculosis* H37rv is partially digested with the restriction endonuclease SalI by reacting 0.03 U of enzyme per μg of DNA in a 100 mM NaCl, 50 mM $MgCl_2$, 1 mM dithiothreitol buffer for 1 hour at 37° C. The genomic DNA thus digested is separated by electrophoresis on 0.6% agarose gel, the fragments between 30 and 40 kb electroeluted and ethanol precipitated after phenol/chloroform (1/1) extraction.

The vector is the cosmid pHC79. It is digested in the same manner and dephosphorylated to avoid any autoligation.

The ligation is carried out by mixing 700 ng of vector and 1.5 μg of 30/40-kb DNA fragments (that is a vector/insert molar ratio of 1/2) and the reaction is left at 14° C. for 18 h after adding 2.5 U of T4 DNA ligase in a 0.066M Tris-HCl buffer, pH 7.5, 5 mM $MgCl_2$, 5 mM dithiothreitol, 1 mM ATP.

The recombinant cosmids are packaged in vitro and used for transforming the bacteria HB 101. The transformed bacteria are incubated for 1 h at 37° C. in an LB medium and then plated on a selective agar medium containing 25 μg/ml of ampicillin. The ampicillin-resistant colonies are all tested for their sensitivity to tetracyclin; indeed, the 30/40-kb DNA fragment is inserted in the vector so as to inactivate the gene for resistance to tetracyclin (Tet) and to preserve the gene for resistance to ampicillin (Amp).

b) Screening of the library and determination of the sequence

A minipreparation of DNA from the first 150 ampicillin-resistant ($Amp^r$) and tetracyclin-sensitive ($Tet^s$) transformant colonies is carried out according to the alkaline lysis technique. The DNA of these preparations is then digested with the restriction endonuclease SalI, analysed by electrophoresis on a 0.6% agarose gel and then transferred onto a nylon filter. The DNA is irreversibly fixed by exposing to UV at 254 nm for 5 min.

These various filters are hybridised for 16 to 18 hours at 68° C. in a mixture containing a 6×SSC buffer (1×SSC corresponds to 0.15M NaCl and 0.015M Na citrate), 10% dextran sulphate, 5× Denhardt's (a 1× Denhardt's solution corresponds to 0.02% of Ficoll, 0.02% of polyvinylpyrrolidone and 0.02% of bovine serum albumin), 10 mM EDTA, 0.5% SDS, 100 μg/ml of salmon sperm DNA; to this mixture are added either total genomic DNA from *M. tuberculosis* H37rv, or total genomic DNA from *M. bovis*-BCG phosphorus 32-radiolabelled by multipriming.

After hybridisation, the filters are washed twice for 10 min with 2×SSC buffer at 65° C., once for 30 min with 2×SSC buffer+0.1% SDS at 65° C. and finally once for 10 min with 0.1×SSC buffer at 65° C. While still wet, the filters are subjected to autoradiography at −80° C. using an intensifying screen for 1 h to 2 days.

The results of these hybridisations have made it possible to isolate the cosmid clone containing a fragment of about 1 kb which hybridises very strongly to the labelled DNA from *M. tuberculosis* H37rv and weakly with the labelled DNA from *M. bovis*-BCG (FIG. 1).

Figure 2:
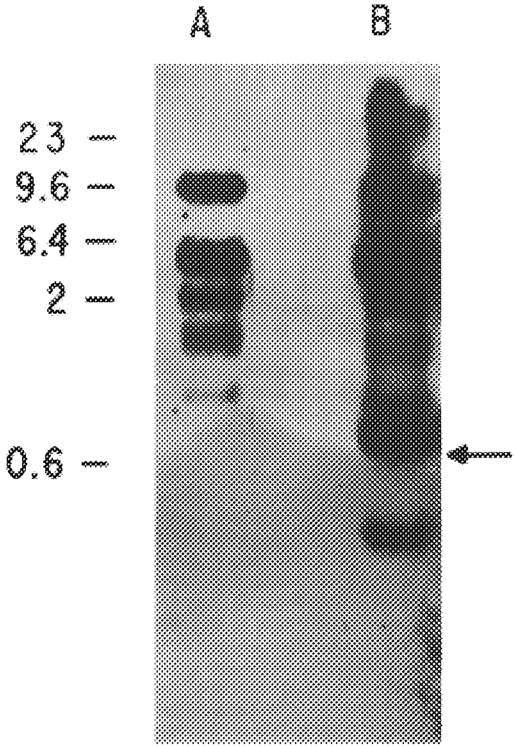
FIG. 2 is a depiction of an autoradiograph of SalI-digested, electrophoresed cosmid clones after Southern blot analysis by hybridizing with labelled genomic DNA from *M. bovis* BCG and *M. tuberculosis*, wherein lane A corresponds to *M. bovis* BCG and lane B corresponds to *M. tuberculosis*, and the arrow indicates the *M. tuberculosis*-specific fragment.

FIG. 2 represents an autoradiograph, after Southern blot analysis, of the cosmid clone using $^{32}P$-labelled DNAs: lane A corresponds to *M. bovis*-BCG; lane B corresponds to *M. tuberculosis*; the arrow shows the *M. tuberculosis*-specific fragment.

This fragment was cloned in a pUC18 vector and prepared in a large amount. This plasmid is called pMT01.

This fragment was digested using the enzymes HindIII, KpnI, SmaI and using a SmaI/HindIII double digestion and then cloned in the phages M13mp18 and M13mp19 and sequenced according to the Sanger method using Taq polymerase in the presence of d-azaGTP instead of dGTP.

The whole sequence of the fragment is represented by formula III above.

Comparison of the first 1152 bases of the sequence thus determined with the entire Los Alamos data bank reveals more than 50% homology with the insertion sequence IS3411 (ISHIGURO et al., J. Bacteriol. 170, 198, 1902–1906). The homology was detected between nucleotides 330 and 1151.

Two 20-mer oligonucleotides inside this homologous sequence were synthesised:

ISTB1 (SEQ ID NO:4): ATGTCAGGTGGTTCATCGAG (formula I above)

ISTB2 (SEQ ID NO:5): ACAGGCCGAGTTTGGTCATC (formula II above)

c) Labelling of the plasmid pMT01 with 2-acetylaminofluorene (AAF)

25 $\mu$g of plasmid pMT01 were labelled using a procedure adapted from that by TCHEN et al. (PNAS 81: 1984; 3466–3470). The level of substitution obtained was 9.7%.

d) Preparation of mycobacteral DNA 1 ml of culture was centrifuged for 5 min at 15000 r/min, the pellet resuspended in 200 $\mu$l of sterile water and subjected to sonication in a sonicating bath for 10 min. The preparation obtained was extracted twice with a phenol/chloroform mixture and then precipitated with ethanol. The DNA pellets obtained were resuspended in 50 $\mu$l of sterile water.

e) Amplification of the DNA

The amplification was carried out using the in vitro amplification technique according to SAIKI et al. (Science, 1988, 239, 487–491) using 12.5 pmol of the oligonucleotides ISTB1 and ISTB2 and 50 ng of DNA from the various mycobacterial strains, in particular the oligonucleotides TB1 and TB2 such as described in Patent Application 89 05057, with 2 U of Taq polymerase in a 50 mM KCl, 10 mM Tris-HCl buffer, pH 8.3, 1.5 mM $MgCl_2$, 125 $\mu$M of deoxyribonucleotides and 100 $\mu$g/ml of gelatine, the final reaction volume being 100 $\mu$l. The parameters of the PCR steps were chosen as follows: 2 min at 94° C., 2 min at 60° C., 2 min at 72° C. 40 cycles are performed using for example the apparatus described in French Application No. 88 08536 filed by the Institut Pasteur. After the final cycle, the samples are maintained at 72° C. for 10 min and then stored at 4° C.

f) Sample analysis

1. Using agarose gel

Figure 3:
FIG. 3 shows various profiles of mycobacterial DNA's amplified using oligonucleotides ISTB1 and ISTB2.

10 $\mu$l of the amplified samples are placed on a 2% agarose gel in a TBE buffer and containing 1 $\mu$g/ml of ethidium bromide. The amplified bands are visualised under UV. FIG. 3 shows the various profiles obtained according to the mycobacterial DNAs. A DNA fragment corresponding to the expected size is observed with DNAs from the following mycobacteria: *M. tuberculosis* (13), *M. bovis*-BCG (16). In contrast, this fragment is not visible when the DNA analysed is extracted from the following strains: *Mycobacterium asiaticum* (1), *M. avium* (2), *M. chelonae* (3), *M. flavescens* (4), *M. gordonae* (5), *M. kansasii* (6), *M. malmoense* (7), *M. marinum* (8), *M. scrofulaceum* (9), *M. simiae* (10), *M. szulgai* (11), *M. terrae* (12), *M. xenopi* (14), Nocardia (15), *Streptomyces antibloticus* (17), *S. lividans* (18), *S. viridochromogene* (19), *S. hydroscopicus* (20), *S. fradiae* (21), Micromonospora (22), *Escherichia coli* (23).

This fragment may, where appropriate, be detected by hybridisation to a probe corresponding to all or part of IS6110. The DNA is then transferred onto a membrane and the procedure carried out as described in b) above.

2. Using dot blot analysis

10 $\mu$l of the amplified samples are denatured by heating at 95° C. for 2 min in 0.2 ml of 0.4M NaOH containing 25 mM EDTA and then rapidly cooled on ice before being placed in the wells of a filtration apparatus fitted with a nitrocellulose membrane.

After washing the wells with 100 $\mu$l of SSPE, the membrane is heated at 80° C. for 1 hour. The filter is hybridised for 16 to 18 hours at 68° C. to the AAF-labelled PMT01 plasmid. After the washings, the immunoenzymatic visualisation is carried out according to the technique described by MASSE et al. (Annales de l'Institut Pasteur/Immunology 136D, 231–243). Only the species belonging to the tuberculosis bacillus group produce a signal on the membrane.

EXAMPLE 2

Figure 4:
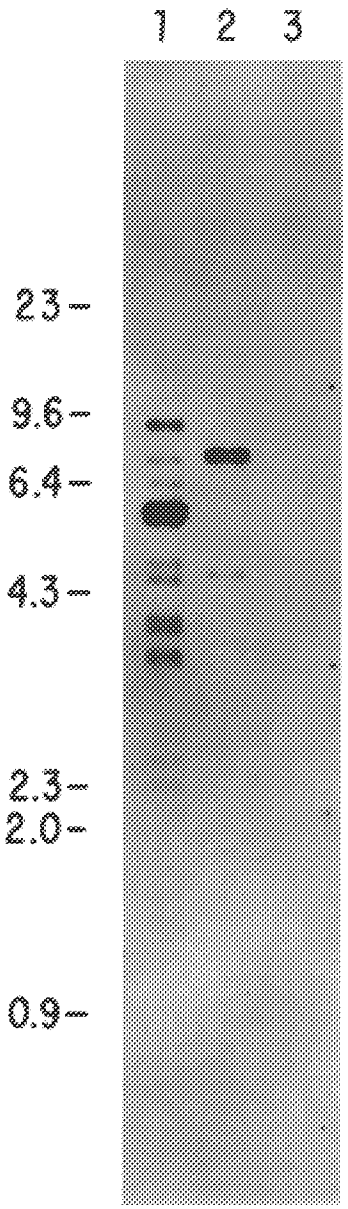
FIG. 4 shows the identification of mycobacterial species by hybridization using the plasmid pMT01 after immunodetection of the hybrids formed, where 14 fragments are observed for a strain of *M. tuberculosis* (lane 1), two fragments for *M. bovis* BCG (lane 2), and no fragments are observed for a strain of M. avium (lane 3)

Identification of the Various Species within the Tuberculosis Bacillus Group After culturing using suitable techniques, the DNAs are extracted as described in paragraph 1d. A total digestion is carried out with the enzyme PstI. These DNAs are then subjected to electrophoresis on a 0.6% agarose gel in TAE before being transferred onto a nitrocellulose membrane according to the Southern technique. A hybridisation performed under the conditions described above and using the plasmid pMT01, or a plasmid derived from it, labelled with acetylaminofluorene, makes it possible, after immunodetection of the hybrids formed, to identify the mycobacterial species as shown in FIG. 4 where 14 fragments are observed for a *M. tuberculosis* strain (lane 1) and only 2 fragments for *M. bovis*-BCG (lane 2), whereas no fragment is observed in lane 3 (*M. avium*).

FIG. 1 represents the location of the various primers and probes of formulae IV to XVI in the sequence IS6110, while their positions with respect to the complete sequence of formula III are represented in FIG. 8.

Figure 5A:
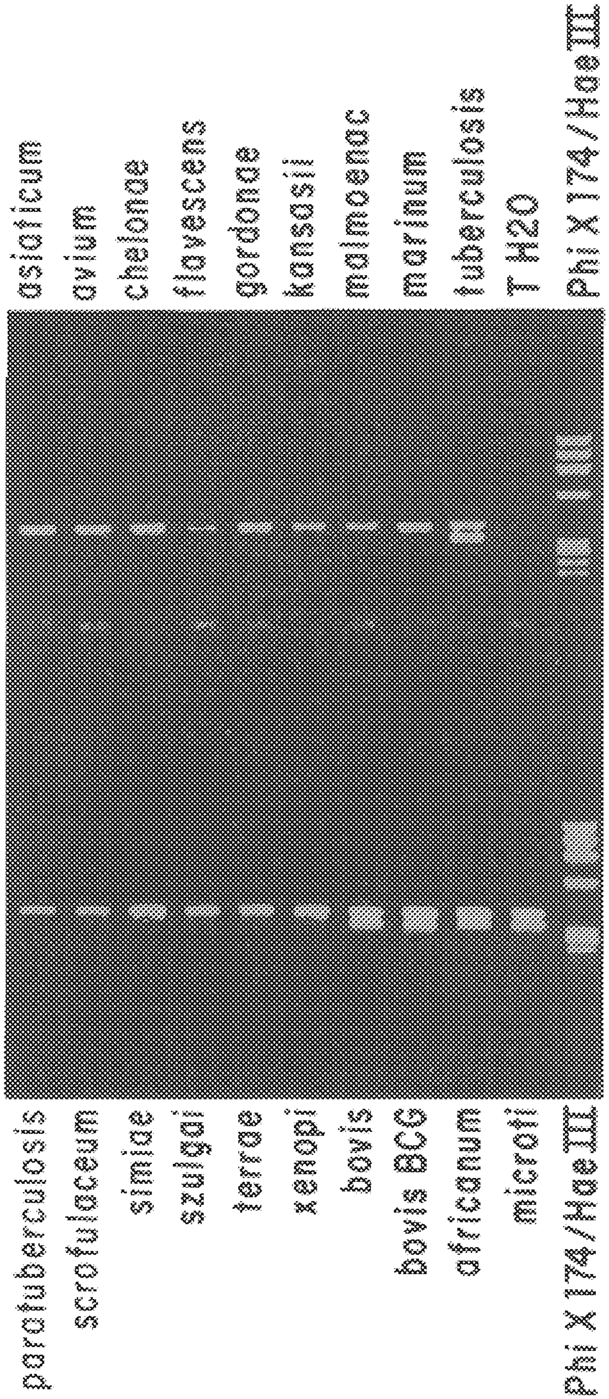
FIG. 5*a* represents the specificity of amplification using the primer pair ISTB2/ISTB7.

FIG. 5*a* represents the specificity of amplification of the pair ISTB2/ISTB7 : purified RNA of 19 mycobacterial species was amplified using two pairs of primers:

- the pair STB1/STB2 allowing the amplification of a fragment (383 bp) of the gene encoding the 65-kD mycobacterial protein,
- the pair ISTB2/ISTB7,
- mycobacteria of the tuberculosis group exhibit a positive amplification with the two pairs whereas atypical mycobacteria are detected only by the pair TB1/TB2.

Figure 5B:
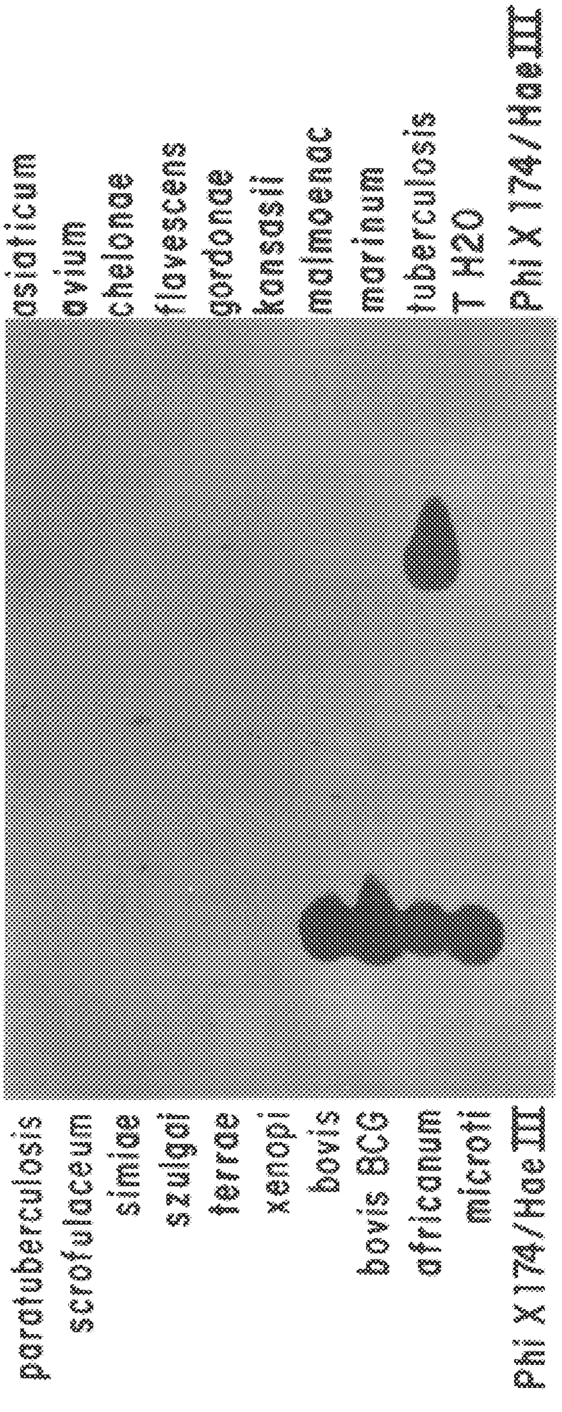
FIG. 5*b* represents the hybridization of the probe IS-2 to the fragment amplified using primer pair ISTB2/ISTB7.

FIG. 5*b* represents the hybridisation of the probe IS-2 to the fragment amplified from ISTB2/ISTB7.

Figure 6:
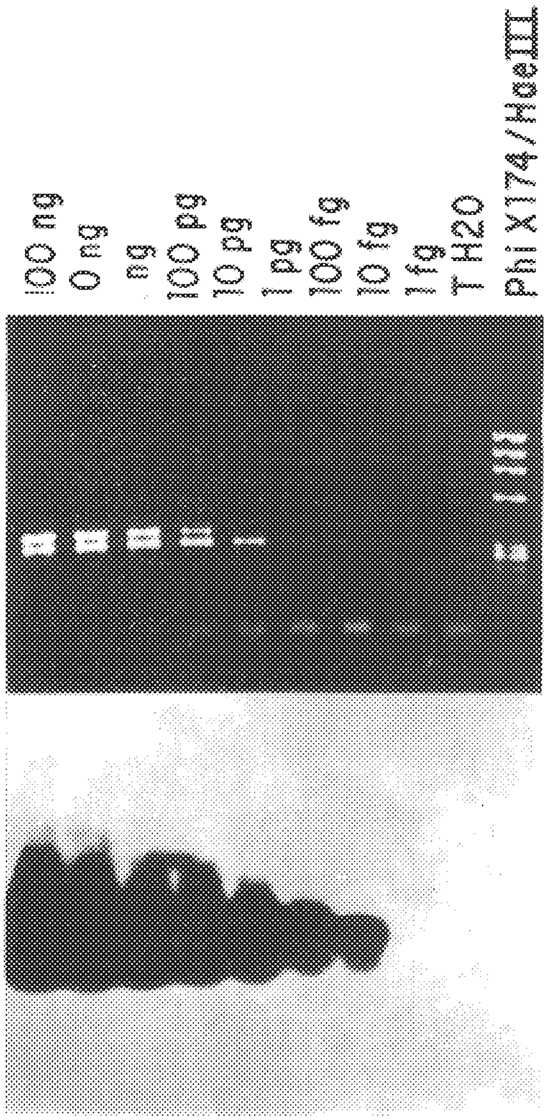
FIG. 6 represents the sensitivity of the amplification detection using the primer pair ISTB2/ISTB7 and the hybridization to the probe IS-2.

FIG. 6 represents the sensitivity of the amplification detection using the pair ISTB2/ISTB7 and the hybridisation to the probe IS-2.

Up to 10 fg of *M. tuberculosis* DNA can be detected, which corresponds to about three bacteria.

EXAMPLE 3

Test for the Detection of *M. tuberculosis* in Clinical Samples

Clinical samples from a variety of sources were treated in accordance with the conditions described by A. BRISSON-NOEL et al., (THE LANCET, 1989, ii: 1069–1071). A fraction of the DNA preparation obtained was amplified using the primers ISTB1/ISTB2 which are specific for the 65-kD antigen and the primers ISTB5/ISTB6 which are specific for the sequence IS6110. The detection was carried out by hybridisation to the probe IS-4. The results obtained are consistent with the clinical and microbiological data, and with the results obtained after hybridisation to a probe which is specific for the 65-kD *M. tuberculosis* gene.

Experimental Conditions a) Amplifications

The amplification reactions are carried out according to the method of Saiki et al., (SCIENCE, 1988, 239, 787–491) using the following reaction mixture:

50 mM KCl, 10 mM Tris-HCl pH 8.3, 1.5 mM $MgCl_2$,

125 $\mu$M deoxyribonucleotides, 12.5 pmol oligonucleotide primers, 50 ng DNA, in a final volume of 100 $\mu$l.

The temperature cycles used are as follows:

2 min at 95° C., 2 min at 60° C., and 2 min at 72° C., for 40 cycles, followed by 5 min at 72° C.

b) Labelling of the probes

The probes were labelled by incorporating radioactive phosphorus ($^{32}P$) into their 5' end using polynucleotide kinase: 25 pmol of oligonucleotide probe were incubated in the presence of Tris-HCl, pH 7.5 (50 mM), $MgCl_2$ (10 mM); dithiothreitol (5 mM); 2.5 ml of ($\gamma^{32}P$)-ATP (specific activity>3000 Ci/mmol) and 2 units of polynucleotide kinase.

c) Hybridisation

The amplified samples were placed on an agarose gel and transferred onto a nylon membrane using conventional techniques (Maniatis). The hybridisations were performed using the Amersham rapid hybridisation buffer as follows: prehybridisation for 15 min at 65° C., hybridisation for 2 hours at 65° C. in the presence of $10^6$ cpm of probe, washes twice for 10 min in 2 SSC/0.1% SDS at 20° C. and once for 15,min in 1 SSC/0.1% SDS at 65° C.

d) Preparation of mycobacterial DNA 1 ml of culture was centrifuged for 5 min at 15,000 r/min, the pellet resuspended in 200 $\mu$l of sterile water and subjected to sonication in a sonicating bath for 10 min. The preparation obtained was extracted twice with a phenol/chloroform mixture and then precipitated with ethanol. The DNA pellets obtained were resuspended in 50 $\mu$l of sterile water.

e) Sample treatment

The samples are not decontaminated before the treatment. A 200 $\mu$l aliquot is placed in an Eppendorf tube, centrifuged and the pellet is resuspended in 200 $\mu$l of lysis solution (NaOH 0.1N, NaCl 2M, SDS 0.5%). After incubating for 15 min at 95° C., two phenol/chloroform extractions and one ethanol precipitation are carried out. The DNA pellet is resuspended in 50 $\mu$l of sterile water. The volume used for the amplification is 5 $\mu$l.

This diagnostic method can be applied to low DNA levels, and it is therefore advantageous for carrying out early and rapid diagnoses.

f) Evaluation on clinical samples (Table I)

41 clinical samples were analysed using the primers ISTB2/ISTB7 and the probe IS-2. The same samples were tested at the same time using conventional techniques (direct examination and culturing):

16 samples which were positive in culture were found to be positive by amplification, 18 samples which were negative in culture were found to be negative by amplification, 1 sample which was weakly positive in culture was found to be negative by amplification; the inventors showed, using an amplification internal standard (simultaneous amplification of a plasmid added to the amplification mixture), that this sample contains inhibitors of the amplification reaction. In contrast to the results obtained with other samples which also contained inhibitors, successive dilutions of this sample remained negative, 6 samples which were negative in culture were found to be positive by amplification. These results do not correspond to false positives as the samples were derived from patients effectively having tuberculosis, the diagnosis having been based on the existence of other samples which were positive in culture, or on histobiological analyses. These results show the excellent sensitivity of the test described in the present application, compared with conventional techniques.

TABLE I

Comparison of the results of DNA amplification with the data for the standard procedures

| | Results of the standard procedures | | |
|---|---|---|---|
| Results PCR | Direct examination positive Culture positive | Direct examination negative Culture positive | Direct examination negative Culture negative |
| Positive for *M. tuberculosis* | | | |
| Serum | 1 | 0 | 0 |
| Expectoration | 2 | 0 | 0 |
| Tubage | 10 | 1 | 0 |
| Cephalorachidian liquid | 0 | 2 | 0 |
| Cystotomy | 0 | 0 | 3 |
| Pleural liquid | 0 | 0 | 2 |
| Biopsy of the liver | 0 | 0 | 1 |
| Negative for *M. tuberculosis* | | | |
| Tubage | 0 | 1 | 15 |
| Cephalorachidian liquid | 0 | 0 | 2 |
| Ganglionic biopsy | 0 | 0 | 1 |

Direct examination: Microscopic examination after Ziehl-Neelssen staining; Culture: Culture on Loewenstein-Jensen solid medium.

Figure 7:
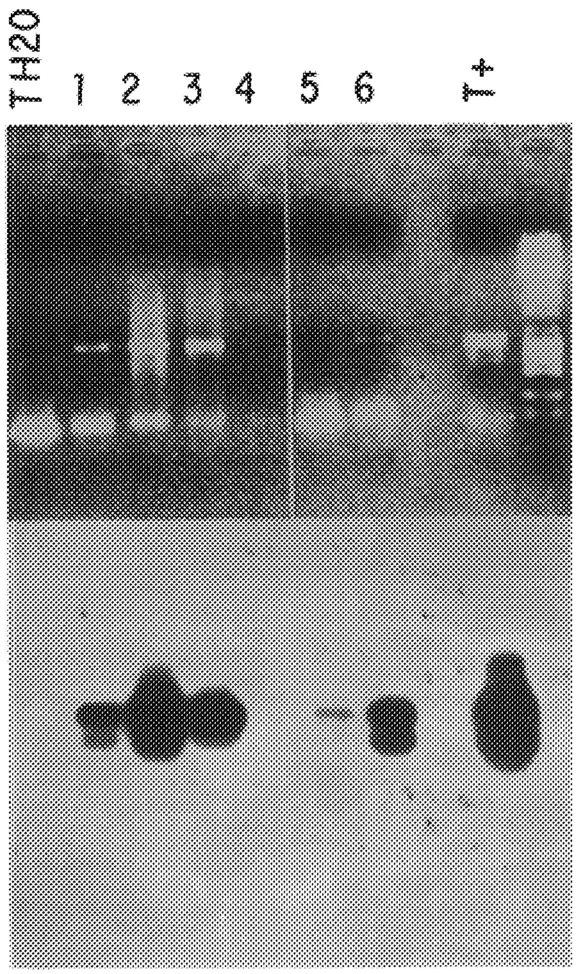
FIG. 7 represents the detection of *M. tuberculosis* in various clinical samples.

FIG. 7 represents the detection of *M. tuberculosis* in the clinical samples:

1. tubage (positive in culture),
2. bronchial aspiration (positive in microscopic examination and in culture),
3. tubage (positive in microscopic examination and in culture),
4. tubage (negative in culture),
5. cephalorachidian liquid (positive in culture),
6. tubage (positive in culture).

As evident from the above, the invention is not in the least limited to the implementation, embodiments and applications which have just been described more explicitly; on the contrary, it embraces all the variants which may come to the mind of a specialist in this field without departing from the framework or the scope of the present invention.

We claim:

1. An isolated polynucleotide of the formula 5'-(SEQ ID NO:1)-(nucleotides 343–1152 of SEQ ID NO:3)-(SEQ ID NO:2)-3'.

2. An isolated polynucleotide of the formula 5'-(SEQ ID NO:1)-(nucleotides 327–1684 of SEQ ID NO:3)-(SEQ ID NO:2)-3'.

3. An isolated polynucleotide of the formula 5'-(SEQ ID NO:1)-(SEQ ID NO:3)-(SEQ ID NO:2)-3'.

4. The isolated polynucleotide of claim 1, which when labelled with $^{32}P$ and hybridized to DNA of *Mycobacterium tuberculosis,* provides a visible spot after autoradiography for about 1 hour, and when labelled with $^{32}P$ and hybridized to DNA of *Mycobacterium bovis* BCG, provides a visible spot after autoradiography for 48 hours and wherein after said hybridization, 14 fragments are observed for *M. tuberculosis* H37RV and 2 fragments are observed for *M. bovis* BCG.

5. The isolated polynucleotide of claim 2, which when labelled with $^{32}P$ and hybridized to DNA of *Mycobacterium tuberculosis,* provides a visible spot after autoradiography for about 1 hour, and when labelled with $^{32}P$ and hybridized to DNA of *Mycobacterium bovis* BCG, provides a visible spot after autoradiography for 48 hours and wherein after said hybridization, 14 fragments are observed for *M. tuberculosis* H37RV and 2 fragments are observed for *M. bovis* BCG.

6. The isolated polynucleotide of claim 3, which when labelled with $^{32}P$ and hybridized to DNA of *Mycobacterium tuberculosis,* provides a visible spot after autoradiography for about 1 hour, and when labelled with $^{32}P$ and hybridized to DNA of *Mycobacterium bovis* BCG, provides a visible spot after autoradiography for 48 hours and wherein after said hybridization, 14 fragments are observed for *M. tuberculosis* H37RV and 2 fragments are observed for *M. bovis* BCG.

7. A recombinant plasmid, comprising the DNA of claim 1.

8. A recombinant plasmid, comprising the DNA of claim 2.

9. A recombinant plasmid, comprising the DNA of claim 3.

10. The plasmid of claim 9, further comprising a vector obtained from pUC18.

11. The plasmid pMT01, deposited under the No. I-900 on Aug. 25, 1989, in the Collection Nationale de Cultures de Microorganisms.

* * * * *